United States Patent [19]

Chu

[11] 4,420,418
[45] Dec. 13, 1983

[54] PARA-SELECTIVE ZEOLITE CATALYSTS

[75] Inventor: Chin-Chiun Chu, North Brunswick, N.J.

[73] Assignee: Mobil Oil Corporation, New York, N.Y.

[21] Appl. No.: 322,629

[22] Filed: Nov. 19, 1981

[51] Int. Cl.$^3$ .................. B01J 37/10; B01J 29/28; B01J 27/18
[52] U.S. Cl. ......................................... 502/77; 502/85
[58] Field of Search ........................... 252/455 Z, 437

[56] References Cited

U.S. PATENT DOCUMENTS

| | | | |
|---|---|---|---|
| 3,493,490 | 2/1970 | Plank et al. | 208/120 |
| 3,684,738 | 8/1972 | Chen | 252/412 |
| 3,972,832 | 8/1976 | Butter et al. | 252/437 |
| 4,002,698 | 1/1977 | Kaeding | 260/671 M |
| 4,034,053 | 7/1977 | Kaeding et al. | 260/672 T |
| 4,274,982 | 6/1981 | Chu | 252/455 Z |

FOREIGN PATENT DOCUMENTS 30796 6/1981 European Pat. Off. .
344444 8/1981 European Pat. Off. .

Primary Examiner—Carl F. Dees
Attorney, Agent, or Firm—Alexander J. McKillop; Michael G. Gilman; Edward F. Kenehan, Jr.

[57] ABSTRACT

A process is provided for treating modified ZSM-5 type zeolite catalysts with carboxylic acid (or anhydride) and water vapor treating agents in order to enhance the para-selective properties of such catalysts for the alkylation of aromatic materials without significantly diminishing catalyst activity. The modified zeolites so treated are those which contain a minor proportion of a difficulty reducible oxide such as magnesium oxide, calcium oxide and/or phosphorus oxide. Such catalyst compositions can be used in alkylation processes to provide alkylated aromatic product mixtures having exceptionally high concentrations of the para-dialkylbenzene isomer.

10 Claims, No Drawings

PARA-SELECTIVE ZEOLITE CATALYSTS

BACKGROUND OF THE INVENTION

1. Field of the Invention

The present invention relates to the preparation and use of modified zeolite catalyst compositions which are especially suitable for the alkylation of aromatic hydrocarbons to provide product mixtures enriched in the para-(or 1,4-)dialkyl substituted benzene isomer.

2. Description of the Prior Art

Production of dialkyl substituted benzene compounds via alkylation of aromatic hydrocarbons is an important step in a number of commercial chemical manufacturing processes. Such reactions can be carried out over a variety of catalyst materials. Alkylation of aromatic hydrocarbons utilizing crystalline aluminosilicate catalysts has, for example, been described. U.S. Pat. No. 2,904,697 to Mattox refers to alkylation of aromatic hydrocarbons with an olefin in the presence of a crystalline metallic aluminosilicate having uniform openings of about 6 to 15 Angstrom units. U.S. Pat. No. 3,251,897 to Wise describes alkylation of aromatic hydrocarbons in the presence of X or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g., benzene with ethylene, in the presence of a ZSM-5 type zeolite catalyst.

In many of these prior art processes, the dialkylbenzene product produced frequently contains more of the 1,3 isomer than of the other two isomers. For example, xylene produced via the conventional catalytic methylation of toluene can have the equilibrium composition of approximately 24 percent of 1,4-, 54 percent of 1,3- and 22 percent of 1,2-isomer. Of the dialkylbenzene isomers, 1,3-dialkylbenzene is often the least desired product, with 1,2- and 1,4-dialkylbenzene being the more useful products. 1,4-Dimethylbenzene, for example, is of particular value, being useful in the manufacture of terephthalic acid which is an intermediate in the manufacture of synthetic fibers such as "Dacron". Furthermore, 1,4-methylethylbenzene, i.e., para-ethyltoluene (PET), is useful for subsequent conversion to para-methylstyrene, and for this purpose ethyltoluene products containing as much as 97% of the para isomer can be required.

Mixtures of dialkylbenzene isomers, either alone or in further admixture with ethylbenzene, have previously been separated by expensive superfractionation and multistage refrigeration steps. Such processes, as will be realized, involve high operation costs and have a limited yield. Alternatively, various modified zeolite catalysts have been developed to alkylate toluene with a greater or lesser degree of selectivity to 1,4-dialkylbenzene isomers. Hence, U.S. Pat. Nos. 3,972,832, 4,034,053, 4,128,592, and 4,137,195 disclose particular zeolite catalysts which have been treated with compounds of phosphorus and/or magnesium to increase para-selectivity of the catalysts. Para-selective boron-containing zeolites are shown in U.S. Pat. No. 4,067,920 and para-selective, antimony-containing zeolites in U.S. Pat. No. 3,979,472. Similarly, U.S. Pat. Nos. 3,965,208; 4,117,026; 4,259,537; 4,260,843; 4,275,256; 4,276,437; 4,276,438; 4,278,827 and 4,288,647 all disclose other zeolites modified with various oxides to improve catalyst para-selectivity.

Notwithstanding the existence of such chemically-modified zeolite catalysts, methods have also been developed to treat such catalysts in an effort to enhance their para-selectivity properties even further. Thus, for example, European Patent Application No. 80304118.5, published June 24, 1981, discloses a process whereby para-selectivity of oxide modified ZSM-5 type zeolite catalysts can be improved by treating such selectivated catalysts with a carboxylic acid such as acetic acid. While such procedures are effective in enhancing catalyst selectivity, catalyst treatment with such materials may sometimes deactivate the catalyst and result in a decrease in conversion when such selectivated catalysts are employed in aromatics alkylation reactions. There is thus a continuing need to develop catalyst preparation procedures which provide highly para-selective zeolite-based catalysts but which do not significantly deactivate the catalyst as a consequence of improved catalyst selectivity.

Accordingly, it is an object of the present invention to provide modified zeolite catalyst compositions which promote the alkylation of aromatics to produce mixtures containing an exceptionally high percentage, e.g., 80% by weight or more for alkylation to toluene, of para-dialkylbenzene isomer.

It is a further object of the present invention to provide methods of preparing such highly para-selective catalysts without significantly reducing catalyst activity.

It is a further object of the present invention to provide highly para-selective alkylation processes employing the modified zeolite catalysts described herein.

SUMMARY OF THE INVENTION

The present invention relates to a process for treating modified zeolite catalysts to render such catalysts highly para-selective for the alkylation of aromatic compounds to produce dialkyl substituted benzene compounds. The zeolite component of the catalysts so treated is one which has a silica to alumina mole ratio of at least 12 and a constraint index within the approximate range of 1 to 12. Such zeolite catalysts are further modified by incorporation thereinto of a minor proportion of a difficultly reducible oxide.

In accordance with the present invention, such catalysts are first contacted with a carboxylic acid or anhydride thereof at a temperature of from about 0° C. to 100° C. to improve catalyst para-selectivity. As a second step, such catalysts are thereafter further contacted with water vapor at a temperature of from about 40° C. to 700° C. to restore catalyst activity which may have been lost in the carboxylic acid or anhydride selectivation treatment. The present invention also relates to modified catalyst compositions treated in this manner and to alkylation processes utilizing such treated modified catalyst compositions.

DETAILED DESCRIPTION OF THE INVENTION

The catalysts which are treated in accordance with the method of the present invention are zeolite based catalysts which promote the alkylation of aromatic compounds. One essential component of such catalysts is a particular type of crystalline zeolite material which exhibits unusual properties. Although these zeolites have unusually low alumina contents, i.e. high silica to alumina mole ratios, they are very active even when the silica to alumina mole ratio exceeds 30. Such activity is surprising, since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g., of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by turning carbonaceous deposits with oxygen-containing gas such as air.

An important characteristic of the crystal structure of this particular class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the intracrystalline free space.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having substantially higher silica/alumina ratios, e.g. 70 and above or even 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also to be included within this definition are substantially pure silica forms of the useful zeolites described herein, that is to say those zeolites having no measurable amount of aluminum (silica to alumina mole ratio of infinity) but which otherwise embody the characteristics disclosed.

Members of this particular class of zeolites, after activation, acquire an intracrystalline sorption capacity for normal hexane which is greater than that for water, i.e. they exhibit "hydrophobic" properties. This hydrophobic character can be used to advantage in some applications.

The zeolites of the particular class useful herein have an effective pore size such as to freely sorb normal hexane. In addition, their structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which may be operative.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of about 1 to 12. Constraint Index (CI) values for some typical materials are:

| Zeolite | C.I. |
| --- | --- |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than a exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The particular class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. Nos. 3,702,886 and Re 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 is more particularly described in published European Patent Application No. 80 300,463, the entire content of which is incorporated herein by reference.

It is to be understood that by incorporating by reference the foregoing patents to describe examples of specific members of the specified zeolite class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratio discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired.

Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article Zeolite Structure by W. M. Meier. This paper, the entire contents of which are incorporated herein by reference, is included in Proceedings of the Conference on Molecular Sieves, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used as precursors to the alkaline-earth metal modified zeolites of the present invention. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing aromatics alkylation processes using the treated catalyst of the present invention, it may be useful to incorporate the above-described crystalline zeolites with a matrix comprising another material resistant to the temperature and other conditions employed in such processes. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

A second essential component of the alkylation catalysts treated in accordance with the present invention comprises a minor proportion, e.g., from about 0.05% to 50% by weight of the catalyst composite, of a difficultly reducible oxide. Oxides of this type can include oxides of phosphorus as well as those oxides of the metals of Groups IA, IIA, IIIA, IVA, VA, IA, VIIA, VIIIA, IB, IIB, IIIB, IVB, or VB of the Periodic Chart of the Elements (Fisher Scientic Company, Catalog No. 5-702-10) which serve to enhance the para-selectivity properties of the catalysts modified therewith. The difficultly reducible oxides most commonly employed to modify the selectivity properties of the zeolite-based catalysts herein are oxides of phosphorus and magnesium. Thus, the catalysts herein can be treated with phosphorus and/or magnesium compounds in the manner described in U.S. Pat. Nos. 3,894,104; 4,049,573; 4,086,287; and 4,128,592, the disclosures of which are incorporated herein by reference.

Phosphorus, for example, can be incorporated into such catalysts at least in part in the form of phosphorus oxide in an amount of from about 0.25% to about 25% by weight of the catalyst composition, preferably from about 0.7% to about 15% by weight. Such incorporation can be readily effected by contacting the zeolite composite with a solution of an appropriate phosphorus compound, followed by drying and calcining to convert the phosphorus in the zeolite to its oxide form. Preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchlorothiophosphate, methyl acid phosphate and other alcohol-$P_2O_5$ reaction products. Particularly preferred are ammonium phosphates, including ammonium hydrogen phosphate, $(NH_4)_2HPO_4$, and ammonium dihydrogen phosphate, $NH_4H_2PO_4$. Calcination is generally conducted in the presence of oxygen at a temperature of at least about 150° C. However, higher temperatures, i.e., up to about 500° C. or higher are preferred. Such heating is generally carried out for 3–5 hours but may be extended to 24 hours or longer.

Magnesium oxide is another preferred difficultly reducible oxide which can be incorporated with the zeolite composites in a manner similar to that employed with phosphorus. Magnesium can comprise from about 0.25% to 25% by weight preferably from about 1% to 15% by weight present at least in part as magnesium oxide. As with phosphorus, magnesium oxide incorporation is effected by contacting the zeolite composite with an appropriate magnesium compound followed by drying and calcining to convert magnesium in the zeolite to its oxide form. Preferred magnesium-containing compounds include magnesium nitrate and magnesium acetate. Calcination times and temperatures are generally the same as recited hereinbefore for calcination of phosphorus-containing catalysts.

In addition to treatment of the zeolite composites to incorporate phosphorus and/or magnesium oxides as hereinbefore described in detail, such zeolites may also be modified in a substantially similar manner to incorporate a variety of other oxide materials to enhance para-selectivity. Such oxide materials include oxides of boron (U.S. Pat. No. 4,067,920); antimony (U.S. Pat. No. 3,979,472); beryllium (U.S. Pat. No. 4,260,843); Group VIIA metals (U.S. Pat. No. 4,275,256); alkaline earth metals (U.S. Pat. No. 4,288,647); Group IB metals (U.S. Pat. No. 4,276,438); Group IVB metals (U.S. Pat. No. 4,278,827); Group VIA metals (U.S. Pat. No. 4,259,537); Group IA elements (U.S. Pat. No. 4,329,533); cadmium (U.S. Ser. No. 139,611, filed Apr. 11, 1980), iron and/or cobalt (U.S. Ser. No. 150,868, filed May 19, 1980); Group IIIB metals (U.S. Pat. No. 4,276,437); Group IVA metals (U.S. Pat. No. 4,302,620); Group VA metals (U.S. Pat. No. 4,302,621); and Group IIIA elements (U.S. Pat. No. 4,302,622).

Treatment of the zeolite catalysts to incorporate any of the foregoing oxide materials to enhance para-selectivity while maintaining activity will generally occur before such catalysts are treated with carboxylic acid and moisture treating agents of the present invention in order to provide even greater enhancement of the para-selective properties of such catalysts. Additional catalyst modifying procedures which may also optionally be employed to modify catalyst activity or para-selectivity include precoking and presteaming (i.e., before oxide incorporation), or combinations thereof.

In accordance with the present invention, the oxide modified, para-selective, zeolite-based catalyst composites as hereinbefore described are treated in a two-step operation to enhance para-selectivity, i.e., to either to restore diminished para-selectivity or improve inherent para-selectivity, without significantly diminishing catalyst activity. In the first step of such treatment, the oxide-modified, zeolite-based catalyst composite is contacted with a carboxylic acid or an anhydride thereof under conditions which enhance catalyst para-selectivity. Such a carboxylic acid can contain from 2 to about 5 carbon atoms and can be either linear or branched. Examples of suitable carboxylic acids for use in the heating method of the instant invention include acetic acid, propanoic acid, butanoic acid, pentanoic acid, 2-methylpropanoic acid, 2,2-dimethylpropanoic acid, 2-methylbutanoic acid, 3-methylbutanoic acid, and the like. Acetic acid and acetic anhydride are the preferred catalyst treating agents.

The carboxylic acid or anhydride may be either in the vapor phase or in the liquid phase when used to treat the catalyst. If in the vapor phase, treatment is preferably carried out by passing a stream of air or nitrogen or other gaseous substance (argon, methane, pentane, etc.) which has been saturated with the carboxylic acid across the modified catalyst for a period of time ranging from about 1 hour to about 20 hours. During contact with the acid vapors, the catalyst is maintained at a temperature of from about 0° C. to about 100° C., preferably at from 15° C. to 100° C. and most preferably at a temperature of between 20° C. and 50° C.

When treatment is carried out using liquid carboxylic acid, the modified catalyst is immersed in the acid for from 5 minutes to 24 hours at a temperature as recited above with respect to vapor phase treatment. The liquid may comprise substantially pure carboxylic acid (e.g. glacial acetic acid) or may contain diluents or carriers admixed with the acid. Examples of diluents utilizable for this purpose would include aromatic and non-aromatic hydrocarbons, alcohols, water, dimethylformamide, and other liquid materials which are inert with respect to the acid and the zeolite. After immersion for a sufficient period of time to enhance the para-selectivity of the catalyst, the liquid can be removed and the catalyst can be dried at from about 90° C. to about 150° C. to remove all traces of the liquid.

The amount of carboxylic acid employed is not critical so long as carboxylic acid contact with the catalyst serves to enhance para-selectivity of the catalyst being treated. Generally, catalyst is contacted with at least about 0.02 grams of acid (or anhydride) per gram of catalyst per hour. Preferably at least about 0.05 grams of carboxylic acid per gram of catalyst per hour can be employed.

After the catalyst has been treated with carboxylic acid or anhydride in the foregoing manner, the treated catalyst may optionally be calcined in conventional manner. Such calcination generally involves contacting the catalyst with an atmosphere maintained at a temperature of from about 200° C. to 1000° C. for a period of from about 0.5 to 24 hours or longer. Calcination generally is conducted in an atmosphere such as air, nitrogen, helium, etc.

After treatment with carboxylic acid or anhydride, the catalysts described exhibit enhanced selectivity for formation of para-disubstituted aromatic compounds when such catalysts are used to promote alkylation of aromatics. Such an increase in selectivity, however, generally occurs with some loss of catalyst activity. In accordance with the present invention, it has been surprisingly discovered that such a drop in catalytic activity which can occur as a result of catalyst selectivation with carboxylic acid or anhydride can be substantially offset by further treatment of the catalyst with water vapor under certain conditions.

Catalyst contact with water vapor occurs under conditions which serve to enhance the activity of the carboxylic acid or anhydride selectivated but deactivated oxide modified catalyst. Such conditions include a contact temperature of from about 40° C. to 700° C., preferably from about 50° C. to 600° C. Such conditions can also include a water vapor/catalyst contact time of at least about 1 hour, preferably from about 2 to 72 hours.

As with carboxylic acid or anhydride treatment, the amount of water vapor employed is not critical so long as water vapor contact with the catalyst is sufficient to enhance the activity of the treated catalyst with respect to its effectiveness in promoting aromatics alkylation. Thus, generally catalyst is contacted with at least about 0.01 gram of water vapor per gram of catalyst per hour, more preferably with at least about 0.02 gram of water vapor per gram of catalyst per hour. In a preferred method of treating the catalyst herein, air at ambient temperature is saturated with water vapor and is then passed over the catalyst to be treated at the elevated catalyst treatment temperatures recited above.

After water vapor treatment, the modified catalysts of the present invention may optionally again be calcined in conventional manner to render the catalyst suitable for use in promoting aromatics alkylation reactions. Thus, after water vapor treatment is completed to the extent desired, the treated catalyst can be contacted with an atmosphere maintained at a temperature from about 200° C. to 1000° C. for a period of from about 0.5 to 24 hours. Again, calcination is generally conducted in an atmosphere such as air, nitrogen, helium and the like.

It has been surprisingly discovered that treatment of the particular zeolite catalyst composites of this invention with the carboxylic acid and water vapor treating agents in the manner herein described will provide catalysts having enhanced para-selective properties when such catalysts are used to promote the alkylation of aromatic compounds to dialkyl substituted benzene compounds. Such enhancement occurs even with catalysts which are already highly para-selective by virtue of having been treated with a difficultly reducible oxide of, for example, phosphorus, calcium and/or magnesium compounds. Alternatively, treatment of the zeolite catalysts herein in the particular manner of the present invention can permit elimination of the need for steaming and/or precoking procedures in order to reach given levels of para-selectivity, particularly after regeneration of such catalysts with air or other oxygen-containing gas. As noted, such enhancement of the para-selectivity properties of the catalyst herein occurs without a significant loss of catalyst activity as can sometimes occur as a result of catalyst selectivation procedures.

The treated zeolite catalysts of the present invention are advantageously used to promote alkylation of aromatic compounds to provide dialkyl-substituted benzene product mixtures which are highly enriched, in the para-dialkyl substituted benzene isomer. Alkylation of aromatic compounds in the presence of the above-described catalysts can be effected by contact of the aromatic with an alkylating agent. A particularly preferred embodiment involves the alkylation of toluene wherein the alkylating agents employed comprise methanol or other well known methylating agents or ethylene. The reaction is carried out at a temperature of between about 250° C. and about 750° C., preferably between about 300° C. and 650° C. At higher temperatures, the zeolites of high silica/alumina ratio are preferred. For example, ZSM-5 having a $SiO_2/Al_2O_3$ ratio of 30 and upwards is exceptionally stable at high temperatures. The reaction generally takes place at atmospheric pressure, but pressures within the approximate range of $10^5$ N/m$^2$ to $10^7$ N/m$^2$ (1-100 atmospheres) may be employed.

Some ion-limiting examples of suitable alkylating agents would include olefins such as, for example, ethylene, propylene, butene, decene and dodecene, as well as formaldehyde, alkyl halides and alcohols, the alkyl portion thereof having from 1 to 16 carbon atoms. Numerous other aliphatic compounds having at least one reactive alkyl radical may be utilized as alkylating agents.

Aromatic compounds which may be selectively alkylated as described herein would include any alkylatable aromatic hydrocarbon such as, for example, benzene, ethylbenzene, toluene, dimethylbenzene, diethylbenzene, methylethylbenzene, propylbenzene, isopropylbenzene, isopropylmethylbenzene, or substantially any mono- or di-substituted benzenes which are alkylatable in the 4-position of the aromatic ring.

The molar ratio of alkylating agent to aromatic compound is generally between about 0.05 and about 5. For instance, when methanol is employed as the methylating agent and toluene is the aromatic, a suitable molar ratio of methanol to toluene has been found to be approximately 0.1 to 1.0 mole of methanol per mole of toluene. When ethylene is employed as the alkylating agent and toluene is the aromatic, a suitable molar ratio of ethylene to toluene is approximately 0.05 to 2.5 moles of ethylene per mole of toluene.

Alkylation is suitably accomplished utilizing a feed weight hourly space velocity (WHSV) of between about 1 and about 1000, and preferably between about 1 and about 200. The reaction product, consisting predominantly of the 1,4-dialkyl isomer, e.g. 1,4-dimethylbenzene, 1-ethyl-4-methylbenzene, etc., or a mixture of the 1,4- and 1,3-isomers together with comparatively smaller amounts of 1,2-dialkylbenzene isomer, may be separated by any suitable means. Such means may include, for example, passing the reaction product stream through a water condenser and subsequently passing the organic phase through a column in which chromatographic separation of the aromatic isomers is accomplished. Alkylation using the treated modified catalysts of the present invention can provide product mixtures containing at least 80% or even 90% or more by weight of the para-dialkylbenzene isomer.

The alkylation processes described herein may be carried out as a batch type, semi-continuous or continuous operation utilizing a fixed or moving bed catalyst system. The catalyst after use in a moving bed reactor can be conducted to a regeneration zone wherein coke is burned from the catalyst in an oxygen-containing atmosphere, e.g. air, at an elevated temperature, after which the regenerated catalyst can be recycled to the alkylation zone for further contact with the charge stock. In a fixed bed reactor, regeneration can be carried out in a conventional manner where an inert gas containing a small amount of oxygen (0.5-2%) is used to burn the coke in a controlled manner so as to limit the temperature to a maximum of around 500°-550° C.

The following examples will serve to illustrate certain specific embodiments of the hereindisclosed invention. These examples should not, however, be construed as limiting the scope of the invention, as there are many variations which may be made thereon without departing from the spirit of the disclosed invention, as those of skill in the art will recognize.

EXAMPLE I

A typical base catalyst composition illustrating the type of catalyst using in evaluating the various catalyst treating agents and procedures employed in this invention is described as follows. To prepare such a catalyst, $NH_4ZSM-5$ zeolite (200 grams) having a crystal size of about 0.1 micron in the form of 1/16 inch diameter extrudate with a 35 weight percent alumina binder is used. If desired, the catalyst may be presteamed at 500° C. for 1 hour at a gaseous steam rate of 50 ml/min. The catalyst material is then impregnated with a solution of 80 grams of diammonium acid phosphate in 10 ml. of water, dried at 80° C. for about 16 hours in an open dish. The catalyst is then calcined in air at 500° C. for 2 hours to give a phosphorus modified zeolite. The resulting product is cooled, and a 6.0 gram aliquot is impregnated with a solution of 6.0 grams of calcium acetate monohydrate in 10 ml. of water, dried at 80° C. from about 18 hours and calcined in air at 500° C. for 4 hours. The final catalyst contains 2.68 weight percent calcium, present at least in part as the oxide, and 2.8 weight percent phosphorus, present at least in part as the oxide.

EXAMPLE II

A Ca-P-ZSM-5 catalyst of the type described in Example I is used to promote ethylation of toluene. Using a reaction temperature of 400° C. and a WHSV of 7 for toluene and 0.5 for ethylene, a reaction is carried out resulting in 18.6% conversion of toluene to produce an ethyltoluene product containing 86.4% of the para-ethyl toluene isomer. After the reaction, the catalyst is regenerated in air at 500° C.

EXAMPLE III

The catalyst from Example II is then soaked in glacial acetic acid for 15 minutes at ambient temperature. The catalyst is then dried and calcined at 500° C. for 16 hours. Using the same reaction conditions as in Example II, toluene is reacted with ethylene in the presence of such an acetic acid-treated catalyst. Ethylation of toluene gives 7.1% conversion of toluene to produce an ethyltoluene product which contains 92.3% of the para-ethyltoluene isomer.

In can be seen from a comparison of Examples II and III that treatment of the catalyst with acetic acid in the manner described improves the para-selectivity of the catalyst but lowers its activity.

EXAMPLE IV

The deactivated catalyst of Example III is treated by passing through the catalyst bed at the rate of 300 cc/min. a stream of air which has been saturated with water at ambient temperature and then directed into the catalyst bed at 90° C. for 16 hours. The treated catalyst is then calcined in air at 500° C. for 1 hour.

Toluene is again reacted with ethylene in the presence of such a treated catalyst using the reaction conditions of Examples II and III. Ethylation of toluene now gives 19.1% conversion of toluene to produce an ethyltoluene reaction product which contains 94.1% of the para-ethyltoluene isomer.

It can be seen from a comparison of Examples II, III and IV that treatment of the catalyst with both acetic acid and water vapor in accordance with the present invention serves to significantly increase the para-selectivity of the catalyst with no loss of catalyst activity.

What is claimed is:

1. A method for treating a chemically modified zeolite catalyst in order to enhance the para-selectivity of said catalyst without significantly diminishing the activity thereof when said catalyst is utilized to promote alkylation of aromatic compounds, said catalyst comprising both a crystalline zeolite material having a constraint index within the approximate range of 1 to 12 and a silica/alumina mole ratio of at least 12 and a minor proportion of one or more difficulty reducible oxides, said method comprising
   (a) improving the para-selectivity of said catalyst while at the same time lowering the activity of said catalyst by contacting said catalyst with a carboxylic acid containing from 2 to about 5 carbon atoms or an anhydride of such a carboxylic acid at a temperature between about 0° C. and 100° C.; and thereafter
   (b) improving the activity of the catalyst of step (a) without significantly diminishing the para-selectivity of the catalyst of step (a) by contacting said catalyst of step (a) with water vapor at a temperature between about 40° C. and 700° C. for at least about 1 hour.

2. A method for treating a chemically modified zeolite catalyst in order to enhance the para-selectivity of said catalyst without significantly diminishing the activity thereof when said catalyst is utilized to promote alkylation of aromatic compounds, said catalyst comprising both a crystalline zeolite material having a constraint index within the approximate range of 1 to 12 and a silica/alumina mole ratio of at least 12 and a minor proportion of one or more difficulty reducible oxides, said method comprising
   (a) improving the para-selectivity of said catalyst while at the same time lowering the activity of said catalyst by contacting said catalyst with a carboxylic acid selected from acetic acid, propanoic acid, butanoic acid, pentanoic acid, 2-methylpropanoic acid, 2,2-dimethylpropanoic acid, 2-methylbutanoic acid, 3-methylbutanoic acid and anhydrides of said carboxylic acids at a temperature between about 0° C. and 100° C.; and thereafter
   (b) improving the activity of the catalyst of step (a) without significantly diminishing the para-selectivity of the catalyst of step (a) by contacting said catalyst of step (a) with water vapor at a temperature between about 40° C. and 700° C. for at least about 1 hour.

3. A method according to claim 2 wherein said difficultly reducible oxide is selected from magnesium oxide, calcium oxide, phosphorus oxide, combinations of magnesium oxide and phosphorus oxide and combinations of calcium oxide and phosphorus oxide.

4. A method according to claim 3 wherein said carboxylic acid is acetic acid.

5. A method according to claim 4 wherein contact between catalyst and carboxylic acid or anhydride occurs at a temperature of from about 15° C. to 100° C., and contact between catalyst and water vapor occurs at a temperature of from about 50° C. to 600° C.

6. A method according to claim 4 wherein liquid phase acetic acid is contacted with said catalyst.

7. A method according to claim 4 wherein acetic acid vapor is contacted with said catalyst.

8. A process for treating a chemically modified zeolite catalyst in order to enhance the para-selectivity of said catalyst without significantly diminishing the activity thereof when said catalyst is utilized to promote alkylation of aromatic compounds, said catalyst comprising both a crystalline zeolite material selected from ZSM-5, ZS-11, ZMS-12, ZMS-23, ZMS-35, ZMS-38 and ZMS-48 and a minor proportion of one or more difficulty reducible oxides selected from magnesium oxide, calcium oxide, phosphorus oxide, combinations of magnesium oxide and phosphorus oxide and combinations of calcium oxide and phosphorus oxide, said method comprising
   (a) improving the para-selectivity of said catalyst while at the same time lowering the activity of said catalyst by contacting said catalyst with acetic acid or acetic anhydride at a temperature between about 0° C. and 100° C.; and thereafter
   (b) improving the activity of the catalyst of step (a) without significantly diminishing the para-selectivity of the catalyst of step (a) by contacting said catalyst of step (a) with water vapor at a temperature between about 40° C. and 700° C. for at least about 1 hour.

9. A catalyst composition prepared in accordance with the method of claim 1, 2, 3, 4, 5, 6, 7 or 8.

10. A catalyst composition according to claim 9 comprising from about 1 to 99% by weight of zeolite material with the balance of said composition comprising a binder for said zeolite material.

* * * * *